United States Patent [19]

Jendrisak

[11] Patent Number: 6,030,814
[45] Date of Patent: Feb. 29, 2000

[54] REVERSE TRANSCRIPTION METHOD

[75] Inventor: Jerome J. Jendrisak, Madison, Wis.

[73] Assignee: Epicentre Technologies Corporation, Madison, Wis.

[21] Appl. No.: 08/840,474

[22] Filed: Apr. 21, 1997

[51] Int. Cl.[7] ................................................ C12P 19/34
[52] U.S. Cl. ................. 435/91.51; 435/91.1; 435/91.21; 536/22.1; 536/23.1
[58] Field of Search ................. 435/91.1, 91.21, 435/91.51; 536/22.1, 23.1

[56] References Cited

U.S. PATENT DOCUMENTS

| | | |
|---|---|---|
| 5,310,652 | 5/1994 | Gelfand et al. . |
| 5,322,770 | 6/1994 | Gelfand . |
| 5,407,800 | 4/1995 | Gelfand et al. . |
| 5,545,539 | 8/1996 | Miller et al. ............................ 435/91.2 |
| 5,693,517 | 12/1997 | Gelfland et al. ......................... 435/193 |

FOREIGN PATENT DOCUMENTS 44 11 588 C1   9/1995   Germany .

WO 96/12041   4/1996   WIPO .

OTHER PUBLICATIONS

N. Baskaran, et al., "Uniform Amplification of a Mixture of Deoxyribonucleic Acids with Varying GC Content," *Genome Research* 6:633–638, 1996.

D.S. Mytelka and M.J. Chamberlin, "Analysis and suppression of DNA polymerase pauses associated with a trinucleotide consensus," *Nucl. Acids Res.* 24(14):2774–2781, 1996.

W.A. Rees, et al., "Betaine Can Eliminate the Base Pair Composition Dependence of DNA Melting," *Biochemistry* 32(1):137–144, 1993.

T. Weissensteiner and J.S. Lanchbury, "Strategy for Controlling Preferential Amplification and Avoiding False Negatives in PCR Typing," *BioTechniques* 21(6):1102–1108, 1996.

*Primary Examiner*—Kenneth R. Horlick
*Assistant Examiner*—Janell E. Taylor
*Attorney, Agent, or Firm*—Quarles & Brady LLP

[57] ABSTRACT

A method of improving the synthesis of full-length cDNA transcripts by $Mn^{++}$-dependent reverse transcriptases, preferably DNA-dependent DNA polymerases, is disclosed.

9 Claims, No Drawings

REVERSE TRANSCRIPTION METHOD

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION cDNA Synthesis

In the presence of $Mn^{++}$, various DNA-dependent DNA polymerases can act as reverse transcriptases by utilizing RNA as a template and synthesizing a complementary cDNA initiated from an oligonucleotide primer (Karkas, J. D., *Proc. Natl. Acad. Sci. USA* 70:3834–3838, 1973). The reaction is regarded as inefficient when compared to the rate of synthesis, overall yield of cDNA, and abundance of full-length transcripts produced by bona-fide reverse transcriptases such as avian myeloblastosis virus (AMV) or murine Moloney leukemia virus (MMLV) reverse transcriptases (Powell, L. M., et al., *Cell* 50:831–840, 1987).

Thermostable DNA-dependant DNA polymerases acting as reverse transcriptases have been used for cDNA synthesis. Reactions carried out at elevated temperatures (greater than 50° C.) are expected to show increased priming specificity and ability to reverse transcribe through regions of RNA secondary structure compared to mesophilic enzyme reactions. Thermostable DNA polymerases that can be used as reverse transcriptases have also been used in the RT-PCR process to create DNA copies (amplicons) starting with an RNA target (Myers, T. W. and Gelfand, D. H. *Biochemistry* 30:7661–7666, 1991 and U.S. Pat. Nos. 5,322,770; 5,310,652; and 5,407,800).

Betaine

Betaine (N,N,N,-trimethylglycine) has been shown to improve PCR efficiency. U.S. Pat. No. 5,545,539 (Miller, filed Oct. 18, 1994) describes a method of improving the PCR amplification of a target nucleotide sequence by use of an effective amount of a glycine-based osmolyte. The osmolyte reduces the appearance of "stutter bands" in the amplification product, thus allowing for easier detection of the target nucleotide sequence.

Rees et al. (Biochemistry 32:137–144, 1993) demonstrate that betaine has the ability to reduce or eliminate the base pair composition dependence of DNA thermal melting transitions.

DE4411588C1 discloses a buffer for RNA and DNA polymerase reactions containing betaine and the use of the buffer in PCR reactions and in reverse transcription of RNA into cDNA using MMLV reverse transcriptase.

Needed in the art is a method of increasing the overall yield of cDNA and abundance of full-length transcripts in order to improve the sensitivity and quantitative aspects of the overall RT-PCR process.

BRIEF SUMMARY OF THE INVENTION

We have found that betaine improves the synthetic yield of full-length cDNA by thermostable DNA polymerases acting as reverse transcriptase in the presence of $Mn^{++}$.

The present invention is a method of DNA synthesis comprising the steps of exposing an RNA template to a thermostable DNA-dependent DNA polymerase in the presence of an amount of betaine effective to increase reverse transcription. The polymerase reverse transcribes the RNA template and a DNA copy of the template is created. Preferably, the concentration of betaine is between 0.5 and 3.0 M, most preferably 2.0 M (±0.5 M).

The present invention is also a kit for a reverse transcription reaction. In a preferable embodiment, the kit comprises a betaine-containing solution, nucleotides, deoxyribonucleotides and a DNA-dependent DNA polymerase. Preferably, the kit comprises an instruction sheet for the use of thermostable DNA-dependent DNA polymerases in the betaine-containing solution in a reverse transcription reaction.

In another embodiment of the present invention, the method is coupled to an amplification method, most preferably a polymerase chain reaction.

It is an object of the present invention to provide an improved reverse transcription reaction.

It is another object of the present invention to provide a method of increasing the yield and abundance of full-length transcripts in a cDNA synthesis reaction.

It is another object of the present invention to improve the overall quantitative aspects of an RT-PCR process.

Other objects, features, and advantages of the present invention will become apparent after an examination of the specification and claims.

BRIEF DESCRIPTION OF THE SEVERAL VIEWS OF THE DRAWINGS

Not applicable.

DETAILED DESCRIPTION OF THE INVENTION

The present invention is a method of DNA synthesis comprising the step of exposing an RNA template to a thermostable DNA-dependent DNA polymerase in the presence of an amount of betaine effective to increase reverse transcription. The method is applicable to methods of employing DNA-dependent DNA polymerases as reverse transcriptases known to those with skill in the art.

Although the present invention is exemplified by particular DNA polymerases described below, the invention is not limited to these examples. Other thermostable polymerases that have been reported in the literature are useful in the practice of the methods described. Examples of these include polymerases extracted from the thermophilic bacteria *Bacillus stearothermophilus, Thermosipho africanus, Thermotoga maritima*, Thermus species SPS17, *T. brockianus, T. flavus, T. lactues, T. rubens, T. ruber,* and T. species Z05. In addition, thermostable polymerases isolated from the thermophilic archaebacteria include, for example, *Desulfurococcus mobilis, Methanobacterium thermoautotrophicum, Methanothermus fervidus, Pyrococcus furious, Pyrodictium occulturn, Sulfolobus acidocaldariu, S. solfataricus, Thermococcus litoralis,* and *Thermoplasma acidophilum*.

Modified thermostable polymerases may result from proteolytic degradation or may be produced from a truncated gene. These proteins are also useful in the practice of the present invention so long as they function to polymerize deoxyribonucleoside triphosphates using an RNA template.

The method of the present invention is believed to work on any RNA template that could be a substrate for reverse transcription by either reverse transcriptases or DNA polymerases acting as reverse transcriptases.

The examples below describe a typical reverse transcription reaction mixture. A preferred reaction mixture includes RNA template molecules, oligonucleotide primers, a mixture of all four dNTPs, and a suitable buffer. The examples below disclose the use of a buffer comprising 0.01 M Tris-HCl, pH 8.3, 0.05 M KCl, 1.5 mM $MgCl_2$ and 0.75 mM $MnCl_2$. U.S. Pat. Nos. 5,322,770; 5,310,652; and 5,407,800 describe Mn-dependent reverse transcription reactions.

A thermostable DNA polymerase is then added to the reaction mixture. Preferably, the thermostable DNA-dependent DNA polymerases is isolated from either *Thermus thermophilus* or *Bacillus stearothermophilus*. However, polymerases from a variety of other thermostable organisms, as describe above, are also believed to be suitable.

The reaction is incubated in the presence of betaine preferably obtained from Sigma Chemical Company, St. Louis, Mo. as betaine monohydrate, catalog # B2754. Betaine is optimally used at 0.5 to 2.5 M. Concentrations of 2 M (±0.5 M) are preferable. Our experiments show that concentration of betaine at 3 M is at least marginally effective.

The present invention requires that the polymerase reverse transcribe the RNA template in a DNA copy of the template be created. One may detect the presence or absence of this DNA copy by visualization of the reverse transcribed material on an electrophoretic gel.

In the examples below, we were able to increase the amount of synthesized cDNA from unobservable amounts to observable amounts. We envision, however, that the method of the present invention is also applicable to situations in which cDNA synthesis is merely inefficient and not necessarily totally repressed. Any improvement of cDNA synthesis, as defined by at least a 10% increase of product as measured by incorporation of radiolabelled dNTPs into full-length product, is consistent with the present invention.

The present invention is also a kit for performing a reverse transcription reaction by the method of the present invention. In its most basic form, the kit comprises a vial or container of betaine-containing solution or buffer and instructions for the reaction. Preferably, the kit also comprises deoxyribonucleotides and a thermostable DNA-dependent DNA polymerase.

EXAMPLES

A. Experimental

*E coli* ribosomal RNA was used as a target template RNA in a mixture for cDNA synthesis by DNA polymerases isolated from *Thermus thermophilus* and *Bacillus stearothermophilus*. Reaction mixtures containing 1 ug of ribosomal RNA preparation contained 23S, 16S and 5S rRNA species; an oligonucleotide primer which anneals near the 3' end of the 16S rRNA species; a mixture of all four deoxyribonucleoside triphosphates (dATP, dCTP, dGTP and dTTP); a suitable reaction buffer (0.01 M Tris-HCl, pH 8.3, 0.05 M KCl, 1.5 mM $MgCl_2$ and 0.75 mM $MnCl_2$); and 5 units of Tth DNA polymerase or Bst DNA polymerase. The mixture was incubated at 60° C. for 20 minutes in the absence of or presence of various concentrations of betaine (up to 3.0 M). Reaction mixtures were analyzed by 1% agarose gel electrophoresis along with DNA size standards. Nucleic acid bands were visualized by ethidium bromide staining and ultraviolet light (312 nm) transillumination.

B. Results

The banding patterns on the electrophoretic gels indicated that the presence of betaine in the reaction mixtures at concentrations of around 2 M improved the synthesis of cDNA as indicated by the appearance of a strong band migrating at about 1.4 kb. This size is consistent with the size expected for a full-length cDNA/16S rRNA hybrid. In the absence of betaine, no such band was visualized and smaller products predominated in the reaction mixture.

When reaction samples were analyzed by alkaline gel agarose electrophoresis, which results in the destruction of all RNA, a single band of cDNA was observed which migrated at 1.4 kb, again consistent with the synthesis of full-length cDNA. In the absence of betaine, smaller products were again seen on the gel.

The mechanism by which betaine enhances the synthesis of cDNA by TTh and Bst DNA polymerases is unclear. Improvement in RNA stability at elevated temperatures in the presence of $Mn^{++}$, alteration in RNA conformation so that it is better utilized as a template by DNA polymerase, and improved priming are possible factors.

I claim:

1. A method of DNA synthesis comprising the step of exposing an RNA template to a thermostable DNA-dependent DNA polymerase in the presence of an amount of betaine effective to increase reverse transcription, wherein the polymerase reverse-transcribes the RNA template and a DNA copy of the template is created.

2. The method of claim 1 wherein the concentration of betaine is between 0.5 and 3.0 M.

3. The method of claim 2 wherein the concentration is 2.0 M (±0.5 M).

4. The method of claim 1 wherein the thermostable DNA-dependent DNA polymerase is selected from the group consisting of polymerases isolated from *Thermus thermophilus* and *Bacillus stearothermophilus*.

5. The method of claim 1 further comprising the step of amplifying the DNA copy.

6. The method of claim 5 wherein the amplification is a polymerase chain reaction.

7. A kit for reverse transcriptase reaction comprising a container of betaine-containing solution, an aliquot of manganese and instructions for the reverse transcription process.

8. The kit of claim 7 additionally comprising deoxyribonucleotides.

9. The kit of claim 7 additionally comprising an aliquot of a thermostable DNA-dependent DNA polymerase.

* * * * *